United States Patent [19]

Rowles et al.

[11] Patent Number: 4,720,293
[45] Date of Patent: Jan. 19, 1988

[54] PROCESS FOR THE RECOVERY AND PURIFICATION OF ETHYLENE

[75] Inventors: Howard C. Rowles, Center Valley; Kimberly S. Grassi, Schnecksville; Dennis P. Bernhard, Allentown, all of Pa.

[73] Assignee: Air Products and Chemicals, Inc., Allentown, Pa.

[21] Appl. No.: 43,582

[22] Filed: Apr. 28, 1987

[51] Int. Cl.$^4$ ............................................. F25J 1/02
[52] U.S. Cl. .......................................... 62/24; 62/28; 62/31; 62/39; 62/41
[58] Field of Search ................... 62/9, 11, 23, 24, 27, 62/28, 31, 32, 34, 36, 38, 39, 40, 41, 42, 44

[56] References Cited

U.S. PATENT DOCUMENTS

| | | | |
|---|---|---|---|
| 3,675,435 | 7/1972 | Jackson et al. | 62/26 |
| 4,002,042 | 1/1977 | Pryor et al. | 62/28 |
| 4,035,167 | 7/1977 | Starks | 55/57 |
| 4,072,485 | 2/1978 | Becdelievre et al. | 62/23 |
| 4,163,652 | 8/1979 | Gazzi et al. | 62/28 |
| 4,218,229 | 8/1980 | Schuster | 62/28 |
| 4,270,940 | 6/1981 | Rowles et al. | 62/28 |
| 4,272,270 | 6/1981 | Higgins | 62/24 |
| 4,285,708 | 8/1981 | Politte et al. | 62/42 X |
| 4,356,014 | 10/1982 | Higgins | 62/28 |
| 4,368,061 | 1/1983 | Mestrallet et al. | 62/24 X |
| 4,401,450 | 8/1983 | Schramm | 62/13 |
| 4,404,008 | 9/1983 | Rentler et al. | 62/40 X |
| 4,496,381 | 1/1985 | Norenburg | 62/30 |
| 4,504,296 | 3/1985 | Newton et al. | 62/40 X |
| 4,525,185 | 6/1985 | Newton | 62/11 |
| 4,545,795 | 10/1985 | Liu | 62/11 |
| 4,548,629 | 10/1985 | Chiu | 62/24 X |

OTHER PUBLICATIONS

R. L. Rowell, "New Low-Investment Process to Recover Liquids from Refinery Fuel Gas", Oil & Gas Journal, May 10, 1982, pp. 127-131.
W. R. Minton, "Recovering Ethylene from Refinery Gas" Oil & Gas Journal, Oct. 22, 1982, pp. 62-63.
W. Huang, "Cut Demethanizer Energy Costs," Hydrocarbon Processing, Oct. 1980, pp. 105-108.
V. Kaiser et al, "Optimize Demethanizer Pressure for Maximum Ethylene Recovery" Hydrocarbon Processing, Jun. 1979, pp. 115-121.
V. Kaiser et al, "Analyze Mixed Refrigerant Cycles" Hydrocarbon Processing, Jul. 1978, pp. 163-167.

*Primary Examiner*—William E. Wayner
*Assistant Examiner*—Steven E. Warner
*Attorney, Agent, or Firm*—Willard Jones, II; James C. Simmons; William F. Marsh

[57] ABSTRACT

The present invention relates to a process for the recovery of ethylene from a feed gas containing ethane, methane and other light gases, e.g. cracked gas or refinery off-gases, wherein ethylene is condensed in two stages, preferably rectified, and fed to an integrated demethanizer column. Refrigeration for the process is provided by an integrated combination of work expansion of rejected light gases, by vaporization of separated ethane at low partial pressure but high total pressure, and by a mixed refrigerant system. The process results in the separation and purification of ethylene from the feed gas stream while significantly reducing the energy consumption to do so.

17 Claims, 1 Drawing Figure

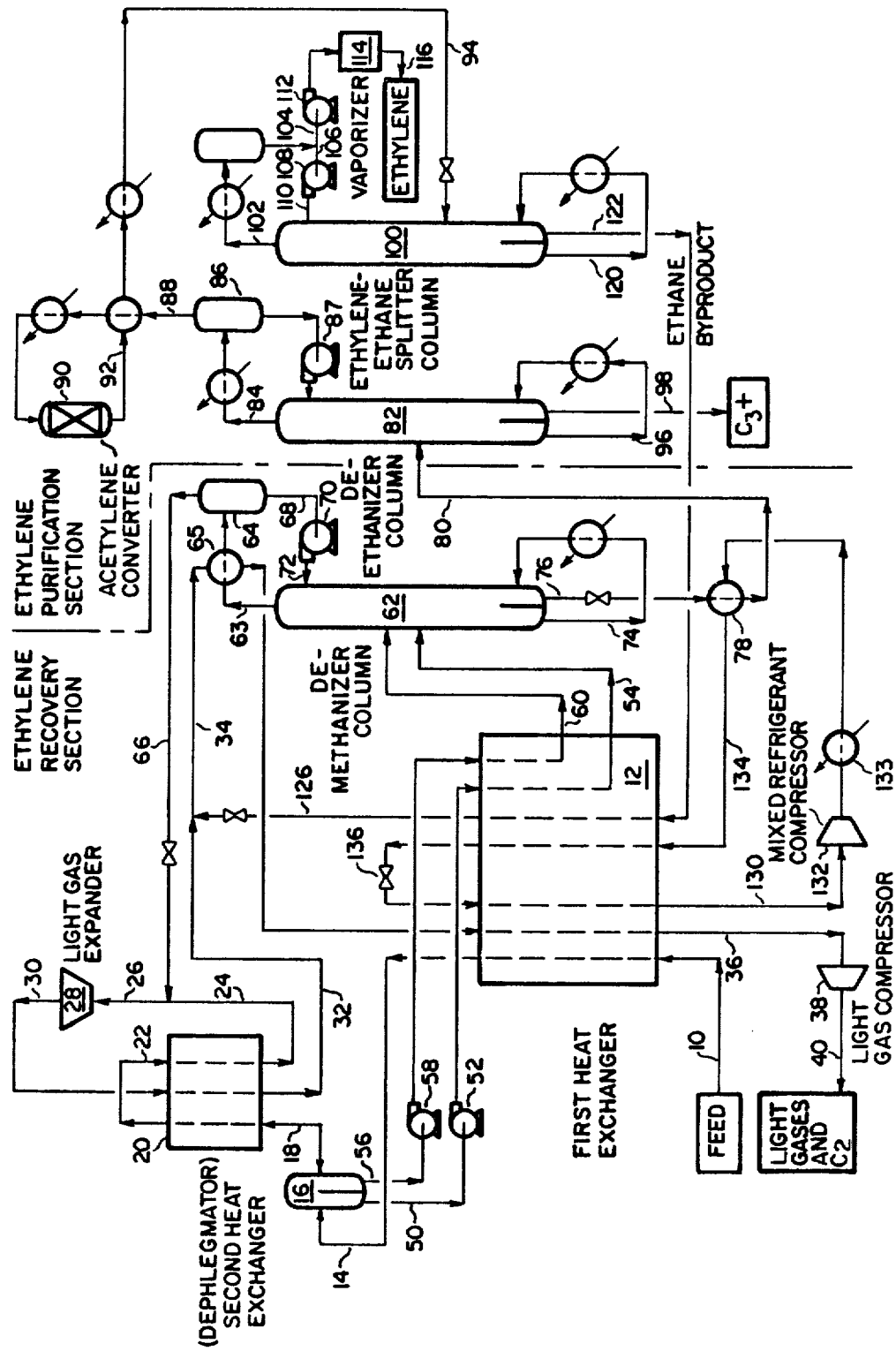

PROCESS FOR THE RECOVERY AND PURIFICATION OF ETHYLENE

TECHNICAL FIELD

The present invention relates to a process for the recovery and purification of ethylene from an ethylene containing feed stream, wherein refrigeration for the ethylene recovery process is provided by an integrated combination of work expansion of rejected light gases, by vaporization of separated ethane at low partial pressure but high total pressure, and by a mixed refrigerant system.

BACKGROUND OF THE INVENTION

In ethylene recovery and purification processes, several methods of refrigeration have been used or proposed in the art. Among these are cascade refrigeration processes, mixed refrigerant processes and expander processes.

Cascade refrigeration systems, usually employing ethylene and propylene refrigerants, are generally used in conventional large scale ethylene plants to recover ethylene from cracked gas. The cascade system provides refrigeration down to about $-150°$ F. Lower level refrigeration is supplied by J-T expansion of methane condensed from the feed gas, sometimes augmented by turbo expanders. Ethane separated from the product ethylene is recycled to the cracking furnaces for conversion to ethylene. Such processes are described in an article by W. Huang in the October 1980 issue of *Hydrocarbon Processing*, page 105–108, and in an article by V. Kaiser, et al, in the June 1979 issue of *Hydrocarbon Processing*, page 115–121, and in U.S. Pat. Nos. 4,496,381; 4,002,042 and 3,675,435.

Mixed refrigerant systems have been proposed to replace the ethylene-propylene cascade systems in conventional ethylene plants. Lower level refrigeration is again supplied by methane and/or turbo expanders. Again, separated ethane is recycled to the cracking furnaces. Such processes are described in an article by V. Kaiser, et al, in the July 1978 issue of *Hydrocarbon Processing*, page 163–167 and in U.S. Pat. No. 4,072,485.

Ethylene recovery processes which rely primarily on expander refrigeration have also been proposed, particularly for recovery of ethylene from refinery gas streams. One such process is described in an article by R. L. Rowell, in the May 10, 1982 issue of *Oil & Gas Journal*, page 127–131. This process is most suitable for low ethylene recovery, e.g. 40 to 80%. This process is also described in U.S. Pat. Nos. 4,272,270 and 4,356,014. The examples given in the patents are specific to C3+ recovery but the claims relate to C2 recovery also. A similar process is described by W. R. Minton in the Oct. 22, 1979 issue of *Oil & Gas Journal*, page 62–63. This process is claimed to be capable of achieving 85% ethylene recovery.

U.S. Pat. Nos. 4,035,167 and 4,401,450 describe processes using solvents, such as hexane or cyclohexane, to recover ethylene from gas mixtures. The latter patent also describes a regenerator process for ethylene recovery. Purification of the recovered ethylene enriched mixture is not discussed in either patent.

SUMMARY OF THE INVENTION

The present invention relates to an improvement to a process for the recovery and purification of ethylene from an ethylene containing feed stream, wherein the ethylene containing feed stream is cooled in two heat exchange stages to condense out the bulk of any ethane and heavier ($C_2+$) material present in the feed stream; the condensed $C_2+$ material is fed to a first distillation column, the demethanizer, to remove any remaining light gases, producing a light gas stream as an overhead of the first distillation column and a demethanized $C_2+$ stream as the bottoms of the first distillation column; the demethanized $C_2+$ stream is then optionally fed to a second distillation column to remove the $C_3+$ portion of the demethanized $C_2+$ stream, producing at least a mixed ethylene-ethane stream as the overhead of the second distillation column and a $C_3+$ stream as the bottoms of the second distillation column; and the mixed ethylene-ethane stream is then preferably fed to an ethylene-ethane splitter column to separate the stream into at least an ethylene product stream and an ethane liquid byproduct stream. The improvement to the process is the provision of low level refrigeration for the second heat exchange stage by work expansion, in one or more stages, of at least a portion of the uncondensed light gas stream removed from the cold end of the second heat exchange stage and, optionally, at least a portion of the light gas stream for the overhead of the first distillation column. Also, the provision of intermediate level refrigeration for the first distillation column condenser and for the cold end of the first heat exchange stage by mixing a liquefied portion of the ethane byproduct stream from the downstream ethylene-ethane separation (or ethylene purification) process with at least part of the light gas stream from the cold end of the second heat exchange stage, or with part or all of the light gas stream from the overhead of the first distillation column, or both. And lastly, provision of high level refrigeration for the warm end of the first heat exchange stage by a mixed refrigerant system.

BRIEF SUMMARY OF THE DRAWING

The single FIGURE of the drawing is a schematic diagram of a preferred embodiment of the process of the present invention.

DETAILED DESCRIPTION OF THE INVENTION

The present invention provides an energy efficient process for recovery and purification of ethylene from a feed gas containing ethane, methane and other light components, such as cracked gas or various types of refinery off-gas. In particular, the present invention provides a process which supplies the refrigeration requirements of the ethylene recovery process with an integrated combination of work expansion of rejected light gases, by vaporization of separated ethane at low partial pressure but high total pressure, and by a mixed refrigerant system. This combination of refrigeration methods is highly energy efficient yet does not result in increased capital costs.

In the process of the present invention, feed gas containing ethylene, ethane and, optionally, heavier hydrocarbons, along with lighter components, is cooled in a first heat exchange stage to condense a large fraction of the $C_2$ and heavier hydrocarbons. The uncondensed vapor is further cooled in a second heat exchange stage to condense most of the remaining $C_2+$ components and achieve high recovery, i.e. at least 90% and preferably 95% or more, of the ethylene, and essentially complete recovery of ethane and heavier components. The first heat exchange stage may consist of one or more heat exchangers, and additional liquid streams may be separated as feeds to the downstream demethanizer column, or for other purposes, such as for removal of the $C_3$ and heavier components. The second heat exchange stage may also consist of one or more heat exchangers, but is preferably a dephlegmator, since the rectification achieved in the dephlegmator minimizes the amount of light components which are condensed with the $C_2^+$ liquids and which must be removed subsequently in a downstream demethanizer column.

The $C_2^+$ liquids condensed in the first and second heat exchange stages are then fed to a demethanizer column, preferable as separate feeds. The $C_2^+$ liquids may be pumped to an elevated pressure, if necessary, such as when the feed gas pressure is below the desirable operating pressure of the demethanizer column. The $C_2^+$ liquids may also be warmed or partially vaporized prior to introduction into the demethanizer column.

In the demethanizer column, residual light components are removed overhead and a demethanized $C_2^+$ liquid stream is recovered from the bottom of the column. The demethanized $C_2^+$ liquid stream is then further separated and purified by any suitable means to recover an ethylene product and, optionally, a $C_3^+$ product, and to reject at least a portion of the ethane as a byproduct stream which ultimately will be used as fuel or for other purposes. Alternatively, the $C_3^+$ components can be rejected with the ethane. Obviously, the $C_3^+$ components could also be removed upstream of the first heat exchange stage, or between the first heat exchange stage and the demethanizer column.

Refrigeration for the ethylene recovery process is provided by a combination of the three methods:

First, low temperature level refrigeration for the second heat exchange stage is provided primarily by work expansion, in one or more stages, of at least a portion of the uncondensed light gas stream removed from the cold end of the second heat exchange stage, usually after partial rewarming. Power from the work expansion of the light gases may be recovered by compressing the feed gas to the process, or by compressing a light gas effluent from the process, or by a generator or other suitable means. At least a portion of the light gas stream from the overhead of the demethanizer column may also be sent to the expander to provide additional low temperature refrigeration.

Second, intermediate level refrigeration for the demethanizer condenser and for the cold end of the first heat exchange stage is provided primarily by mixing a liquefied portion of an ethane byproduct stream from the downstream ethylene-ethane separation process with part or all of the light gas stream from the cold end of the second heat exchange stage, or with part or all of the light gas stream from the overhead of the demethanizer column, or both. The mixed ethane-light gas stream might also supply intermediate level refrigeration to the warm end of the second heat exchange stage. The ethane byproduct stream is preferably liquefied in the downstream ethylene-ethane separation process, but may alternatively be liquefied in the first heat exchange stage.

Refrigeration for the demethanizer condenser is typically required at a temperature level of $-170°$ F. to $-130°$ F., corresponding to an ethane vapor pressure of 3 to 14 psia. Vaporizing a pure ethane liquid to supply refrigeration in this temperature range would require recompression of the ethane vapor from subatmospheric pressure to a pressure suitable for use as fuel or other purposes (e.g. 50 to 150 psia). This recompression from subatmospheric pressure is both undesirable and highly energy intensive. However, by mixing the liquid ethane with a sufficient quantity of light gases, the ethane can be vaporized at low partial pressure in the required temperature range but at a sufficiently high total pressure as to significantly reduce or eliminate recompression. The liquid ethane stream is preferably subcooled prior to mixing with the light gases. The demethanizer condenser may consist of a single overhead condenser, or a combination of an overhead condenser and one or more intermediate or side condensers.

Third, high level refrigeration for the warm end of the first heat exchange stage is provided by a mixed refrigerant system. The mixed refrigerant, consisting primarily of C2, C3 and C4 hydrocarbons, is compressed to a suitable pressure and preferably totally condensed by means of air cooling, cooling water or partial vaporization of the demethanized $C_2^+$ liquid from the bottom of the demethanizer column, or any other suitable means or combination thereof.

The condensed mixed refrigerant stream is preferably subcooled, flashed to a suitable low pressure and revaporized in the first heat exchange stage to provide the required high level refrigeration. Obviously, the mixed refrigerant could be revaporized at several pressure levels to reduce the energy required for recompression of the mixed refrigerant vapor. The mixed refrigerant could also be utilized to provide high level refrigeration for other purposes, such as for precooling the feed gas upstream of the first heat exchange stage, or for providing refrigeration for one or more of the downstream separation and purification steps.

Demethanized $C_2^+$ liquids from the bottom of the demethanizer column may be partially vaporized to condense the mixed refrigerant and processed in a deethanizer column to recover a $C_3^+$ hydrocarbon product, if so desired. The ethylene-ethane overhead from the de-ethanizer column is then preferably separated in a splitter column to provide a high purity ethylene product and a byproduct liquid ethane stream. Obviously, other means for separating and purifying the ethylene in the $C_2^+$ stream could be utilized, e.g. adsorption.

At least a portion of the separated liquid ethane is then subcooled and mixed with the work expanded light gases and then vaporized in the demethanizer column condenser and first heat exchange stage to provide intermediate level refrigeration. The combined ethane-light gas stream may be recompressed in a compressor driven by the light gas expander.

In a preferred mode of operation, the mixed refrigerant is compressed, partially condensed with cooling water or ambient air, and further condensed by partially vaporizing the demethanized $C_2^+$ stream from the bottom of the demethanizer column. The mixed refrigerant is then subcooled, flashed and revaporized at one or more pressure levels to provide high level refrigeration.

The single FIGURE of the drawing depicts a preferred embodiment of the process of the present invention in which both ethylene and $C_3^+$ hydrocarbons are recovered at high purity from a feed gas containing ethane, methane, hydrogen and other light gases. A dephlegmator is utilized as the second heat exchange stage and light gases from the overhead of both the dephlegmator and demethanizer column are work expanded to provide low level refrigeration.

With reference to the single FIGURE of the drawing, feed gas stream 10 containing ethane, methane, hydrogen, and other light gases is cooled in first heat exchanger 12, wherein a portion of the $C_2+$ components are condensed. This mixed phase feed stream is removed from first heat exchanger 12 via line 14 and fed to separator 16. The uncondensed portion of feed stream 14 is then fed to dephlegmator 20, via line 18, wherein the bulk of the remaining $C_2+$ components is condensed. The condensed, rectified $C_2+$ material is removed from dephlegmator 20 and returned to separator 16 via line 18. It should be noted that there is two-way flow in line 18, vapor entering dephlegmator 20 from separator 16 and liquid condensate leaving dephlegmator 20 and returning to separator 16. It should also be noted that separator 16 is constructed so as to segregate the condensates produced in first heat exchanger 12 and in dephlegmator 20, as $C_2+$ liquid streams in lines 50 and 56 respectively.

The uncondensed light gas portion of the feed in line 18 is removed from the cold end (overhead) of dephlegmator 20 via line 22 and warmed in dephlegmator 20 to recover refrigeration. This warmed light gas stream, now in line 24, is mixed with the overhead stream of first distillation column 62, in line 66 to form stream 26. Stream 26 is work expanded in expander 28, returned to dephlegmator 20, via line 30, and warmed to provide additional refrigeration required to operate dephlegmator 20.

The $C_2+$ condensed portions of feed stream 10 in lines 50 and 56 are pumped using pumps 52 and 58, respectively, warmed in first heat exchanger 12, and fed to first distillation column 62 (the demethanizer), via lines 54 and 60, respectively. In first distillation column 62, these two streams are fractionated, an overhead stream is removed via line 63, partially condensed in condenser 65 and separated in separator 64. The liquid portion separated in separator 64, in line 68, is pumped using pump 70 as reflux for column 62, via line 72. The gaseous portion separated in separator 64 is reduced in pressure and mixed with stream 24, via line 66. A portion of the bottom liquid is removed from column 62, via line 74, vaporized and returned to column 62 as reboil. The remaining bottom portion is removed via line 76, reduced in pressure, partially vaporized in heat exchanger 78 and fed to second distillation column 82 (the de-ethanizer), via line 80.

This second column fed in line 80 is then fractioned in second distillation column 82. An overhead stream is removed via line 84, partially condensed and separated in separator 86. The liquid portion separated in separator 86 is pumped using pump 87 as reflux for column 82. The gaseous portion separated in separator 86 is warmed and fed via line 88 to acetylene converter 90. A portion of the bottom liquid is removed from column 82, via line 96, vaporized and returned to column 82 as reboil. The remaining bottom portion is removed as $C_3+$ product via line 98.

The effluent from acetylene converter 90 in line 92 is heat exchanged and fed to ethylene-ethane splitter column 100, via line 94. In splitter column 100, an ethylene stream is removed overhead via line 102, condensed and split into two substreams, in lines 104 and 106. The substream in line 106 is pumped using pump 108 and then returned as reflux to splitter column 100, via line 110. The substream in line 104 is pumped using pump 112 and vaporized in vaporizer 114 to produce an ethylene product in line 116. A portion of the bottom liquid is removed from splitter column 100, via line 120, vaporized and returned to column 100 as reboil. The remaining bottom portion is removed as ethane liquid byproduct via line 122.

The ethane liquid byproduct in line 122 is subcooled in first heat exchanger 12, reduced in pressure and mixed via line 126 with the light gas stream in line 32. The combined ethane byproduct and light gas stream, now in line 34, is heat exchanged in the demethanizer condenser 65 and in first heat exchanger 12 to recover refrigeration and then compressed in compressor 38 to recover the work produced by expander 28 before being removed from the process via line 40.

The mixed refrigerant vapor stream in line 130 is compressed to a higher pressure in compressor 132, cooled and partially condensed in heat excahnger 133 using cooling water or ambient air, and further condensed in heat exchanger 78 by heat exchange with demethanized $C_2+$ liquid from the bottom of the demethanizer column 62. The condensed mixed refrigerant in line 134 is then subcooled in first heat exchager 12, flashed to a lower pressure via valve 136 and revaporized in first heat exchanger 12 before being returned to compressor 132.

As an example, a material balance for selected streams for the process of the present invention as depicted in the single FIGURE of the drawing is provided in Table 1.

TABLE 1

| MATERIAL BALANCE FOR SELECTED STREAMS | | | | | | | | | | | | |
|---|---|---|---|---|---|---|---|---|---|---|---|---|
| | STREAM NUMBER: | | | | | | | | | | | |
| | 10 | 18 | 24 | 26 | 30 | 32 | 34 | 36 | 40 | 50 | 54 | 56 |
| PHASE: | VAP | VAP | VAP | VAP | V & L | VAP | V & L | VAP | VAP | LIQ | V & L | LIQ |
| TEMPERATURE: °F. | 68 | −123 | −155 | −158 | −244 | −136 | −161 | 60 | 110 | −123 | −30 | −134 |
| PRESSURE: PSIA | 290 | 285 | 282 | 282 | 66 | 62 | 62 | 55 | 73 | 285 | 425 | 285 |
| TOTAL FLOW: # MOL/HR | 4211.3 | 3141.2 | 2800.0 | 3015.9 | 3015.9 | 3015.9 | 3671.9 | 3671.9 | 3671.9 | 1070.1 | 1070.1 | 341.2 |
| COMPONENT FLOWS: # MOL/HR | | | | | | | | | | | | |
| HYDROGEN | 1637.3 | 1629.5 | 1626.9 | 1637.3 | 1637.3 | 1637.3 | 1637.3 | 1637.3 | 1637.3 | 7.7 | 7.7 | 2.6 |
| NITROGEN | 229.2 | 224.8 | 223.1 | 229.2 | 229.2 | 229.2 | 229.2 | 229.2 | 229.2 | 4.3 | 4.3 | 1.7 |
| CARB. MONOX. | 24.0 | 23.1 | 22.8 | 24.0 | 24.0 | 24.0 | 24.0 | 24.0 | 24.0 | 0.9 | 0.9 | 0.3 |
| METHANE | 1118.7 | 977.6 | 922.6 | 1118.5 | 1118.5 | 1118.5 | 1118.5 | 1118.5 | 1118.5 | 141.1 | 141.1 | 55.0 |
| ETHYLENE | 450.0 | 156.8 | 4.5 | 6.7 | 6.7 | 6.7 | 8.5 | 8.5 | 8.5 | 293.2 | 293.2 | 152.3 |
| ETHANE | 653.9 | 127.7 | | 0.1 | 0.1 | 0.1 | 653.7 | 653.7 | 653.7 | 526.2 | 526.2 | 127.6 |
| PROPYLENE | 33.8 | 1.1 | | | | | 0.6 | 0.6 | 0.6 | 32.7 | 32.7 | 1.1 |
| PROPANE | 9.4 | 0.3 | | | | | 0.1 | 0.1 | 0.1 | 9.1 | 9.1 | 0.3 |

TABLE 1-continued

MATERIAL BALANCE FOR SELECTED STREAMS

| | | | | | | | | | | | | |
|---|---|---|---|---|---|---|---|---|---|---|---|---|
| BUTANES | 34.0 | 0.2 | | | | | | | | 33.8 | 33.8 | 0.2 |
| PENTANES | 14.2 | | | | | | | | | 14.2 | 14.2 | |
| HEXANES | 6.9 | | | | | | | | | 6.9 | 6.9 | |

| | STREAM NUMBER: | | | | | | | | | | | |
|---|---|---|---|---|---|---|---|---|---|---|---|---|
| | 60 | 63 | 66 | 68 | 76 | 80 | 84 | 88 | 92 | 94 | 98 | 102 |
| PHASE: | LIQ | VAP | VAP | LIQ | LIQ | V & L | VAP | VAP | VAP | LIQ | LIQ | VAP |
| TEMPERATURE: °F. | −80 | −133 | −147 | −147 | 33 | 38 | 20 | 18 | 150 | 8 | 203 | −17 |
| PRESSURE: PSIA | 425 | 400 | 400 | 400 | 400 | 360 | 350 | 350 | 335 | 325 | 350 | 300 |
| TOTAL FLOW: # MOL/HR | 341.2 | 672.5 | 215.9 | 456.6 | 1195.5 | 1195.5 | 1839.5 | 1097.9 | 1097.9 | 1097.9 | 97.6 | 2925.6 |
| COMPONENT FLOWS: # MOL/HR | | | | | | | | | | | | |
| HYDROGEN | 2.6 | 12.0 | 10.3 | 1.7 | | | | | | | | |
| NITROGEN | 1.7 | 9.7 | 6.1 | 3.6 | | | | | | | | |
| CARB. MONOX. | 0.3 | 2.3 | 1.2 | 1.0 | | | | | | | | |
| METHANE | 55.0 | 620.3 | 195.9 | 424.3 | 0.2 | 0.2 | 0.2 | 0.2 | 0.2 | 0.2 | | 1.3 |
| ETHYLENE | 152.3 | 26.3 | 2.2 | 24.1 | 443.3 | 443.3 | 677.1 | 443.3 | 443.3 | 443.3 | | 2923.1 |
| ETHANE | 127.6 | 2.0 | 0.1 | 1.9 | 653.7 | 653.7 | 1160.0 | 653.7 | 653.7 | 653.7 | | 1.2 |
| PROPYLENE | 1.1 | | | | 33.8 | 33.8 | 2.0 | 0.6 | 0.6 | 0.6 | 33.2 | |
| PROPANE | 0.3 | | | | 9.4 | 9.4 | 0.2 | 0.1 | 0.1 | 0.1 | 9.3 | |
| BUTANES | 0.2 | | | | 34.0 | 34.0 | | | | | 34.0 | |
| PENTANES | | | | | 14.2 | 14.2 | | | | | 14.2 | |
| HEXANES | | | | | 6.9 | 6.9 | | | | | 6.9 | |

| | STREAM NUMBER: | | | | | | |
|---|---|---|---|---|---|---|---|
| | 104 | 106 | 116 | 126 | 130 | 134 | 136 |
| PHASE: | LIQ | LIQ | VAP | LIQ | VAP | LIQ | LIQ |
| TEMPERATURE: °F. | −18 | −18 | 86 | −75 | 61 | 50 | −75 |
| PRESSURE: PSIA | 300 | 300 | 667 | 315 | 20 | 220 | 215 |
| TOTAL FLOW: # MOL/HR | 441.9 | 2483.7 | 441.9 | 656.0 | 600.0 | 600.0 | 600.0 |
| COMPONENT FLOWS: # MOL/HR | | | | | | | |
| HYDROGEN | | | | | | | |
| NITROGEN | | | | | | | |
| CARB. MONOX. | | | | | | | |
| METHANE | 0.2 | 1.1 | 0.2 | | | | |
| ETHYLENE | 441.5 | 2481.6 | 441.5 | 1.7 | | | |
| ETHANE | 0.2 | 1.0 | 0.2 | 653.5 | 290.0 | 290.0 | 290.0 |
| PROPYLENE | | | | 0.6 | | | |
| PROPANE | | | | 0.1 | 110.0 | 110.0 | 110.0 |
| BUTANES | | | | | 200.0 | 200.0 | 200.0 |
| PENTANES | | | | | | | |
| HEXANES | | | | | | | |

In this example, refrigeration for columns 82 and 100 condensers in the ethylene purification section of the process is required at two relatively small temperature ranges, e.g. 18° F. and 20° F. and −17° F. to −18° F., respectively, and is most efficiently provided by a single component refrigerant, such as propane, rather than by a mixed refrigerant. Refrigeration for first heat exchanger 12 is required over a larger temperature range, e.g. from +60° F. to −85° F., and is most efficiently supplied by a mixed refrigerant system. In some circumstances, however, refrigeration for the downstream ethylene separation and purification section might be supplied more efficiently by the mixed refrigerant system.

Refrigeration for the ethylene recovery section of the process is required over a very large temperature range, e.g., from ambient to as low as −250° F. This invention utilizes an integrated combination of three refrigeration methods to supply the required refrigeration in a highly energy efficient manner.

Work expansion of part of all of the rejected light gases is utilized to provide low level refrigeration. Part or all of the rejected light gases are combined with a liquefied ethane byproduct from the downstream separation and purification section which can then be vaporized at low partial pressure. but relatively high total pressure, to provide intermediate level refrigeration with little or no energy consumption. A mixed refrigerant system is utilized to provide high level refrigeration. The composition of the mixed refrigerant and the pressure level(s) at which it is revaporized are selected to provide thermodynamically efficient temperature differences between the vaporizing mixed refrigerant stream(s) and the cooling streams in the first heat exchanger. The mixed refrigerant condensing temperature is determined by the available cooling medium, such as ambient air, cooling water, warming or vaporizing process streams, or a combination thereof. This results in a highly energy efficient method for supply of high level refrigeration. A portion of the mixed refrigerant may be revaporized at one or more intermediate pressure levels to further increase the efficiency of the mixed refrigerant system.

The use of three integrated refrigeration methods to supply refrigeration over the very large temperature range required for ethylene recovery results in significant power savings as compared to alternative processes.

Intermediate and high level refrigeration could be supplied by a cascade system of single component refrigerants, such as ethylene and propane or propylene, as is done in conventional ethylene plants. However, this refrigeration is more efficiently supplied by the combination of ethane liquid byproduct revaporization in a mixture with light gases and by a mixed refrigerant system.

Low level refrigeration could be supplied by flashing and vaporization of the impure $C_2+$ liquids condensed in the second heat exchanger. However, the $C_2+$ vapor would then have to be recompressed and reliquefied for processing in the demethanizer column and downstream separation and purification steps. This would result in a very high energy consumption for the recompression. This refrigeration is more efficiently obtained by work expansion of rejected light gases, which are normally required at pressures below the feed gas pressure, such as for delivery to a fuel gas header.

The use of a dephlegmator as the second heat exchanger is preferable, although not required. The rectification achieved in the dephlegmator minimizes the amount of light components which are condensed in the $C_2+$ liquids, which reduces the amount of refrigeration required for the second heat exchanger itself and for the demethanizer column condenser. This provides additional energy savings for the process.

In the example of the single FIGURE of the drawing and Table 1, the overall ethylene recovery and purification process of this invention requires 40% less power than a conventional process utilizing partial condensation in the second heat exchanger, and utilizing work expansion of light gases and a cascade ethylene-propane system for refrigeration supply. This process recovers 98% of the ethylene in the feed gas, at a final purity of 99.9 mole %. It also recovers 98% of the propylene and essentially 100% of propane and heavier hydrocarbons as a $C_3+$ product, with less than 350 ppm of C2 and lighter impurities.

The total power requirement for the process of the present invention, including the downstream $C_3+$ separation and ethylene purification steps, is 3500 HP. The conventional process described above would require over 5800 HP, with significantly higher capital cost. Excluding the downstream separation and purification steps (de-ethanizer and splitter columns), the ethylene recovery section of this invention requires only 1000 HP, as compared to 3300 HP for the conventional process.

The present invention has been described with reference to a preferred embodiment thereof. This description of the preferred embodiment should not be viewed as a limitation on the present invention, but the scope of the present invention should be ascertained by the following claims.

We claim:

1. In a process for the recovery and purification of ethylene from an ethylene containing feed stream, wherein the ethylene containing feed stream is cooled in two heat exchange stages to condense out the bulk of $C_2+$ material present in the feed stream; the condensed $C_2+$ material is fed to a demethanizer column to remove any remaining light gases, producing a light gas stream as an overhead of the demethanizer column and a demethanized $C_2+$ stream is then fed to an ethylene-ethane separation process which produces at least an ethylene product stream and an ethane byproduct stream, the improvement comprising the utilization of three integrated refrigeration cycles wherein low level refrigeration for the second heat exchange stage is provided by work expansion, in one or more stages, of at least a portion of an uncondensed light gas stream removed from the cold end of the second heat exchange stage or an uncondensed light gas stream removed from the cold end of the second heat exchange stage and at least a portion of the light gas stream from the overhead of the demethanizer column; intermediate level refrigeration for the demethanizer column condenser and for the cold end of the first heat exchange byproduct stream from the ethylene-ethane separation process with at least a portion of the light gas stream from the cold end of the second heat exchange stage or at least a portion of the light gas stream from the overhead of the demethanizer column, or both; and high level refrigeration for the warm end of the first heat exchange stage is provided by a mixed refrigerant system.

2. The process according to claim 1 wherein the second heat exchange stage is a dephlegmator which produces a rectified $C_2+$ liquid as a bottoms stream and a cold end light gas streams as an overheated.

3. The process according to claim 2 wherein the $C_2+$ material condensed in the first heat exchange stage and the rectified $C_2+$ liquid condensed in the dephlegmator are fed separately to the demethanizer column.

4. The process according to claim 2 wherein the mixed refrigerant is compressed, condensed, subcooled, and then revaporized in the first heat exchange stage at one or more pressure levels to provide the high level refrigeration.

5. The process according to claim 2 wherein the mixed refrigerant is. compressed, partially condensed with cooling water or ambient air, further condensed by heat exchanger with the demethanized $C_2+$ stream, subcooled and then revaporized in the first heat exchange stage at one or more pressure levels to provide the high level refrigeration.

6. In a process for the recovery and purification of ethylene from an ethylene containing feed stream, wherein the ethylene containing feed stream is cooled in two heat exchange stages to condense out the bulk of $C_2+$ material present in the feed stream; the condensed $C_2+$ material is fed to a distillation column to remove any remaining light gases, producing a light gas stream as an overhead of the distillation column and a demethanized $C_2+$ stream as a bottoms of the distillation column; the demethanized $C_2+$ stream is then fed to an ethylene-ethane splitter column to separate the demethanized $C_2+$ stream into at least an ethylene product stream and a $C_2+$ liquid byproduct stream, the improvement comprising the utilization of three integrated refrigeration cycles wherein low level refrigeration for the second heat exchange stage is provided by work expansion, in one or more more stages, of at least a portion of an uncondensed light gas stream removed from the cold end of the second heat exchange stage or an uncondensed light gas stream removed from the cold end of the second heat exchange stage and at least a portion of the light gas stream from the overhead of the distillation column; intermediate level refrigeration for the distillaton column condenser and for the cold end of the first heat exchange stage is provided by mixing at least a portion of the $C_2+$ liquid byproduct stream for the ethylene-ethane splitter column with at least a portion of the light gas stream from the cold end of the second heat exchange stage or at least a portion of the light gas stream from the overhead of the distillation column, or both; and high level refrigeration for the warm end of the first heat exchange stage is provided by a mixed refrigerant system.

7. The process according to claim 6 wherein the second heat exchange stage is a dephlegmator which produces a rectified $C_2+$ liquid as a bottoms stream and a cold end light gas stream as an overhead.

8. The process according to claim 7 wherein the $C_2+$ material condensed in the first heat exchange stage and the rectified $C_2+$ liquid condensed in the dephlegmator are fed separately to the distillation column.

9. The process according to claim 7 wherein the mixed refrigerant is compressed, condensed, subcooled, and then revaporized in the first heat exchange stage at one or more pressure levels to provide the high level refrigeration.

10. The process according to claim 7 wherein the mixed refrigerant is compressed, partially condensed with cooling water or ambient air, further condensed by heat exchange with the demethanized $C_2+$ stream, subcooled and then revaporized in the first heat exchange stage at one or more pressure levels to provide the high level refrigeration.

11. In a process for the recovery and purification of ethylene from an ethylene containing feed stream, wherein the ethylene containing feed stream is cooled in two heat exchange stages to condense out the bulk of $C_2+$ material present in the feed stream; the condensed $C_2+$ material is fed to a first distillation column to remove any remaining light gases, producing a light gas stream as an overhead of the first distillation column and a demethanized $C_2+$ stream as a bottoms of the first distillation column; the demethanized $C_2+$ stream is then fed to second distillation column to remove the $C_3+$ portion of the demethanized $C_2+$ stream, producing at least a mixed ethylene-ethane stream as an overhead of the second distillation column and a $C_3+$ stream as a bottom of the second distillation column; and the mixed ethylene-ethane stream is fed to an ethylene-ethane splitter column to separate the mixed ethylene-ethane stream into at least an ethylene product stream and an ethane liquid byproduct stream; the improvement comprising the utilization of three integrated refrigeration cycles wherein low level refrigeration for the second heat exchange stage is provided by work expansion, in one or more stages, of at least a portion of an uncondensed light gas stream removed from the cold end of the second heat exchange stage or an uncondensed light gas stream removed from the cold end of the second heat exchange stage and at least a portion of the light gas stream from the overhead of the first distillation column; intermediate level refrigeration for the first distillation column condenser and for the cold end of the first heat exchange stage is provided by mixing at least a portion of the ethane liquid byproduct stream from the ethylene-ethane splitter column with at least a portion of the light gas stream from the cold end of the second heat exchange stage or at least a portion of the light gas stream from the overhead of the first distillation column, or both; and high level refrigeration for the warm end of the first heat exchange stage is provided by a mixed refrigerant system.

12. The process according to claim 11 wherein the second heat exchange stage is a dephlegmator which produces a rectified $C_2+$ liquid as a bottoms stream and a cold end light gas stream as an overhead.

13. The process according to claim 12 wherein the $C_{2+}$ material condensed in the first heat exchange stage and the rectified $C_2+$ liquid condensed in the dephlegmator are fed separately to the first distillation column.

14. The process according to claim 12 wherein the mixed refrigerant is compressed, condensed, subcooled, and then revaporized in the first heat exchange stage at one or more pressure levels to produce the high level refrigeration.

15. The process according to claim 12 wherein the mixed refrigerant is compressed, partially condensed with cooling water or ambient air, further condensed by heat exchange with the demethanized $C_2+$ stream, subcooled and then revaporized in the first heat exchange stage at one or more pressure levels to provide the high level refrigeration.

16. The process according to claim 12 wherein the ethane liquid byproduct is subcooled prior to being mixed with the light gases.

17. The process according to claim 12 wherein the combined ethane-light gas stream is recompressed in a compressor driven by a light gas expander.

* * * * *

UNITED STATES PATENT AND TRADEMARK OFFICE
CERTIFICATE OF CORRECTION

PATENT NO. : 4,720,293

DATED : 19 January 1988

INVENTOR(S) : Howard C. Rowles, Kimberly S. Grassi, Dennis P. Bernhard

It is certified that error appears in the above-identified patent and that said Letters Patent is hereby corrected as shown below:

Column 10, Line 13
    After "exchange", insert -- stage is provided by mixing at least a portion of the liquefied ethane --

Column 10, Line 66
    Delete "for" and substitute therefor -- from --

Signed and Sealed this

Fourteenth Day of June, 1988

Attest:

DONALD J. QUIGG

*Attesting Officer*      *Commissioner of Patents and Trademarks*